(12) United States Patent
Rabenecker

(10) Patent No.: US 6,701,773 B2
(45) Date of Patent: Mar. 9, 2004

(54) PLUG-IN ADAPTER FOR GAS SAMPLING

(75) Inventor: Horst Rabenecker, Stockelsdorf (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 0 days.

(21) Appl. No.: 10/410,465

(22) Filed: Apr. 9, 2003

(65) Prior Publication Data

US 2004/0007048 A1 Jan. 15, 2004

(30) Foreign Application Priority Data

Jul. 12, 2002 (DE) .......................... 102 31 515

(51) Int. Cl.[7] .............................................. G01N 19/10
(52) U.S. Cl. ...................................................... 73/23.2
(58) Field of Search ............................ 73/23.2, 23.27, 73/49.8, 31.05

(56) References Cited

U.S. PATENT DOCUMENTS 4,790,730 A * 12/1988 Spaeth et al. ............... 417/373
5,461,966 A * 10/1995 Becker et al. .................. 92/1
2003/0103851 A1 * 6/2003 Hauser et al. ............... 417/373

FOREIGN PATENT DOCUMENTS

GB          2 105 849          3/1983

* cited by examiner

*Primary Examiner*—Hezron Williams
*Assistant Examiner*—Rodney Frank
(74) *Attorney, Agent, or Firm*—McGlew and Tuttle, P.C.

(57) ABSTRACT

A device for gas analysis with a sensor (5) and a measured gas pump (3). The sensor (5) can be connected in a simple manner both with the suction side (7) or the pressure side (8) of the measured gas pump (3). To accomplish the object, a plug-in adapter (6) is provided, which has a first measuring channel (14) that is in flow connection with the sensor (5), whereby the plug-in adapter (6) can be connected with the measured gas pump (3) in two positions in such a way that a connecting branch (13) of the first measuring channel (14) is connected in a first position of the plug-in adapter (6) on the pressure side (8) and in a second position on the suction side (7) of the measured gas pump (3).

10 Claims, 3 Drawing Sheets

PLUG-IN ADAPTER FOR GAS SAMPLING

FIELD OF THE INVENTION

The present invention pertains to a plug-in adapter for gas sampling for a gas sensor.

BACKGROUND OF THE INVENTION

A device for gas sampling for a gas analyzer has become known from GB 2 105 849 A. The gas is suctioned by means of a pump from the ambient atmosphere and is then fed in a serial sequence to various gas sensors, with which individual gas components can be detected. In this case, the pump works in the so-called pressure operation, in which the gas is suctioned via a flow channel from the ambient atmosphere and then arrives at the sensors behind the pump. The measured gas flows out to the environment via a discharge line. The arrangement of the sensors on the pressure side of the pump is therefore selected because the pressure difference relative to the environment is usually lower on the pressure side of the pump.

However, in some gases, and especially at low gas concentrations, there is the danger that the measured gas component in the pump, which is usually designed as a diaphragm pump, is adsorbed. This effect occurs, e.g., in chlorine and volatile hydrocarbons. In order to minimize the contact with adsorbing materials, such as, e.g., the pump diaphragm, the sensor in these cases is arranged in front of the pump, i.e., on the suction side.

Sensors for the detection of gas components are usually installed in the so-called measuring heads, in which the measuring signals are processed, in order to then display them either on the measuring head itself or on a central evaluation unit. The processing of the measuring signals here includes a calibration and adaptation to the gas type and measuring range. Such measuring heads, which also contain the measured gas pump internally, are usually suitable for accommodating different sensors, which are inserted into the measuring head. Thus, it seems that, depending on the gas component to be-detected, sensors must be arranged either in the, suction area or the pressure area of the measured gas pump.

SUMMARY OF THE INVENTION

The object of the present invention: is to improve a device for gas analysis in such a way that sensors can be arranged in a simple manner on the suction or pressure side of the measured gas pump.

According to the invention, a device is provided for gas analysis with a sensor, a measured gas pump and with a plug-in adapter that can be connected with the measured gas pump and the sensor. The plug-in adapter has a first measuring channel that is in flow connection with a gas-sensitive surface of the sensor. The said plug-in adapter can be connected with the measured gas pump in two positions in such a way that a connecting branch of the first measuring channel is connected in a first position of the said plug-in adapter on the pressure side and in a second position on the suction side of the said measured gas pump.

The advantage of the present invention lies essentially in the fact that a plug-in, adapter, which has a first measuring channel that is in a flow connection with the gas-sensitive surface of the sensor, can be put on the measuring head containing the measured gas pump in two positions. As a result the sensor is located either on the suction side or pressure side of the measured gas pump, depending on the position of the plug-in adapter. The plug-in adapter is preferably designed as an injection molding part, so that all necessary connections can be connected directly with the basic body.

Advantageously, the sensor and the measured gas pump are accommodated in a measuring head, in which case plug sockets for connecting with the suction side and pressure side, as well as the gas-sensitive surface of the sensor, are arranged on a connection surface of the measuring head, which is turned towards the plug-in adapter.

The plug sockets of the measured gas pump and the sensor are positioned on the connection surface of the measuring head in such a way that the plug-in adapter, adapting to any sudden change, can be placed on the measuring head in the two positions.

Advantageously, the plug-in adapter has a measuring channel that can be connected with that plug socket of the measured gas pump that is not occupied -by the first measuring channel. By means of the measuring channels, which are guided on the outside of the plug-in adapter, it is possible to connect hoses to the plug-in adapter, so that a gas sample can also be suctioned and evaluated from a site lying at a remote distance.

It is especially advantageous to provide a switching element on the measuring head that determines the position of the plug-in adapter. The switching element may be designed, e.g., as a microswitch, which is closed in a certain position of the plug-in adapter and which remains in the opened position in another position of the plug-in adapter. This microswitch is connected with an evaluation and control unit of the measuring head, so that it is recognized in the measuring head whether the pertinent type of operation, such as suction operation or pressure operation, is also set for the sensor used.

An exemplary embodiment of the present invention is shown in the figure and is explained in detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
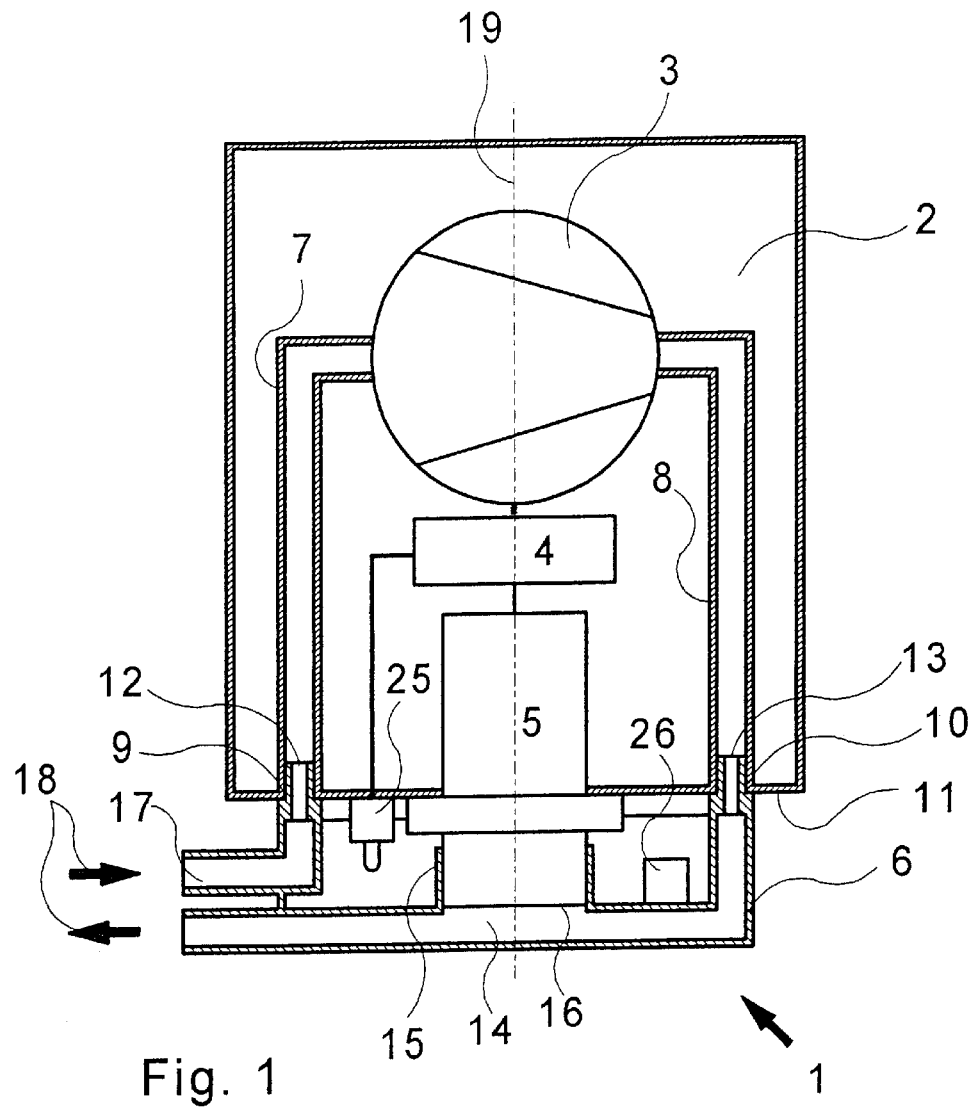
FIG. 1 is a schematic view of a measuring device with a plug-in adapter.

Referring to the drawings in particular, FIG. 1 schematically shows a measuring device 1 for gas analysis, containing a measuring head 2 with a measured gas pump 3, a control and evaluation unit 4 and a sensor 5 and a plug-in adapter 6 installed in the measuring head 2. The measured gas pump 3 feeds the gas sample from the suction side 7 to a pressure side 8, whereby the measured gas pump 3 can be connected with the plug-in adapter 6 via plug sockets 9, 10 on a connection surface 11 of the measuring head 2. To this end, the plug-in adapter 6 has connecting branches 12, 13 which can be introduced into the plug sockets 9, 10. The pressure side 8 is, in terms of flow, connected with a first measuring channel 14 of the plug-in adapter 6, whereby the first measuring channel 14 has a plug-in connection 15 for the sensor 5, so that the gas-sensitive surface 16 of the sensor 5 is in flow contact with the measured gas. A second measuring channel is connected with the suction side 7 via the connecting branch 12. The direction of flow through the plug-in adapter 6 is illustrated by arrows 18. The connecting branches 12, 13 and the plug sockets 9, 10 are arranged symmetrical to a central line 19, so that the plug-in adapter 6 can be placed on the connecting surface 11 of the measuring head in two positions offset by 180°. By means of a push-button switch 25 on the measuring head 2, which is connected with the control and evaluation unit 4, the position of the plug-in adapter 6 can be recognized. To this end, a projection 26 is provided on the plug-in adapter 6, which actuates the push-button switch 25, if it is located below the push-button switch 25.

In the position of the projection 26 shown in FIG. 1, the push-button switch 25 does not send any signal to the control and evaluation unit 4, which is interpreted as pressure operation.

Figure 2:
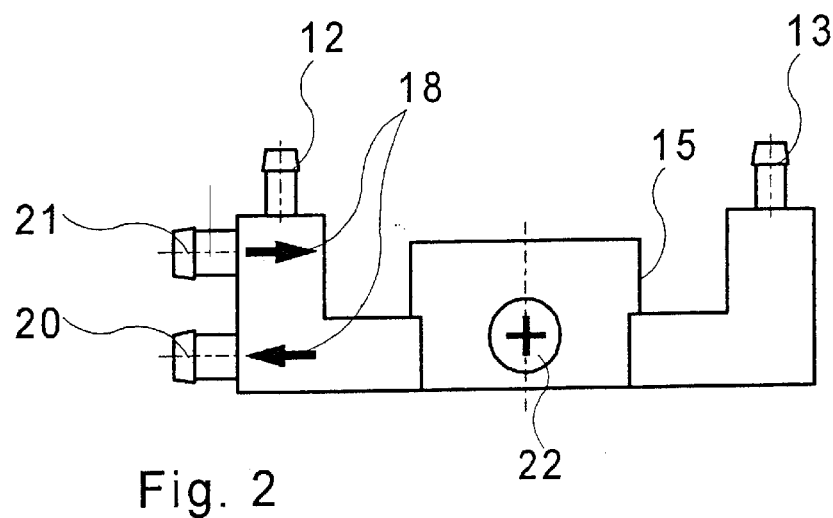
FIG. 2 is a lateral view of the plug-in adapter according to FIG. 1.

FIG. 2 shows the plug-in adapter 6 withdrawn from the measuring head 2. Identical components are provided with the same reference numbers of FIG. 1. The measuring channels 14, 17, in FIG. 1, open into sockets 20, 21, onto which measured gas hoses can be placed. The symbol 22 in the middle of the plug-in adapter 6 stands for pressure operation in this case.

Figure 3:
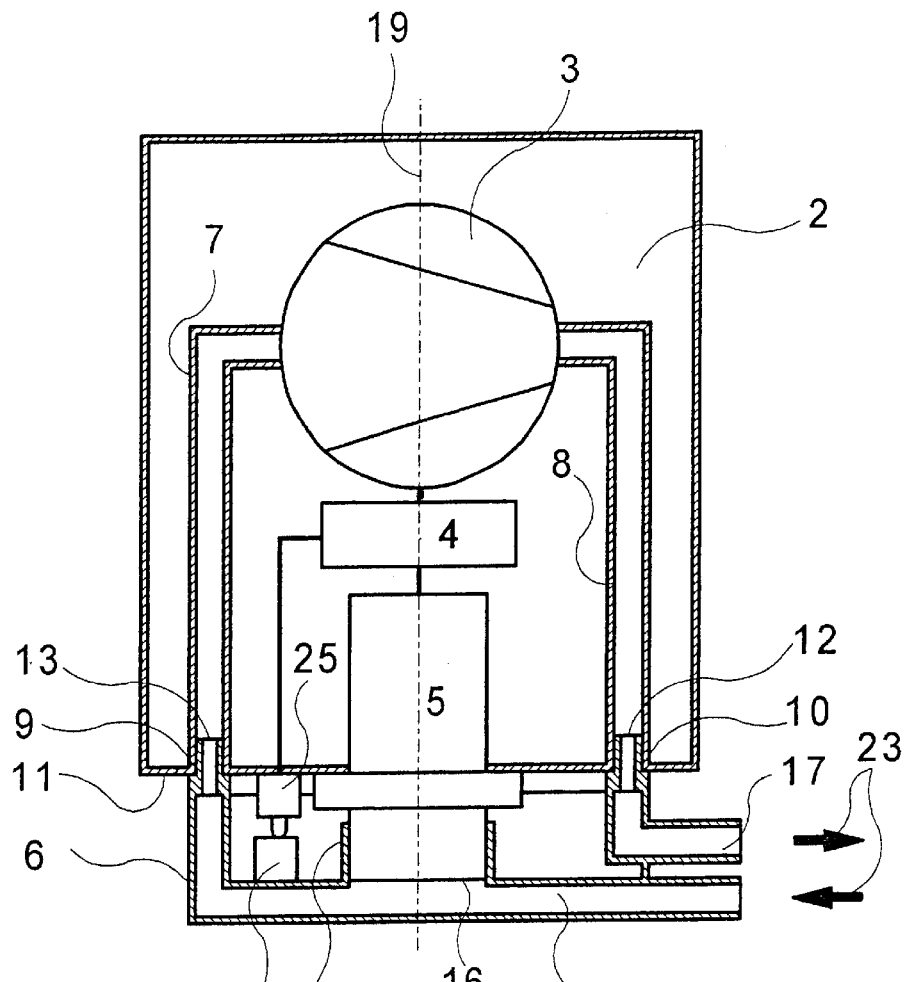
FIG. 3 is a schematic view of the measuring device according to FIG. 1 with the plug-in adapter placed in a second position.

FIG. 3 shows the measuring head 2 with a plug-in adapter 6 placed offset by 180° compared with FIG. 1. Identical components are provided with the same reference numbers of FIGS. 1 and 2. In the mode of operation shown in FIG. 3, the sensor 5 is located on the suction side 7 of the measured gas pump 3. The direction of flow is shown by arrows 23. In this position of the plug-in adapter 6, the projection actuates the switch 25 and the evaluation and control unit 4 recognizes the position of the plug-in adapter 6 in the suction operation.

Figure 4:
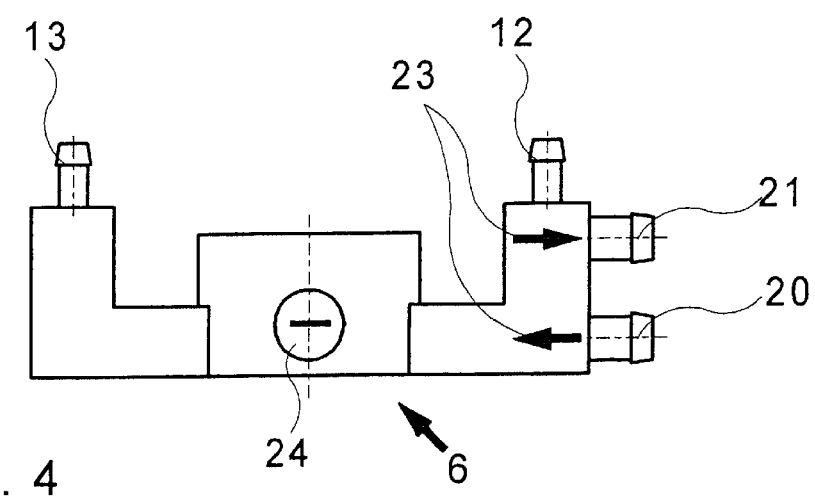
FIG. 4 is a lateral view of the plug-in adapter according to FIG. 3.

FIG. 4 shows the plug-in adapter 6 withdrawn from the measuring head 2, whereby the symbol 24 stands for the suction operation.

Figure 5:
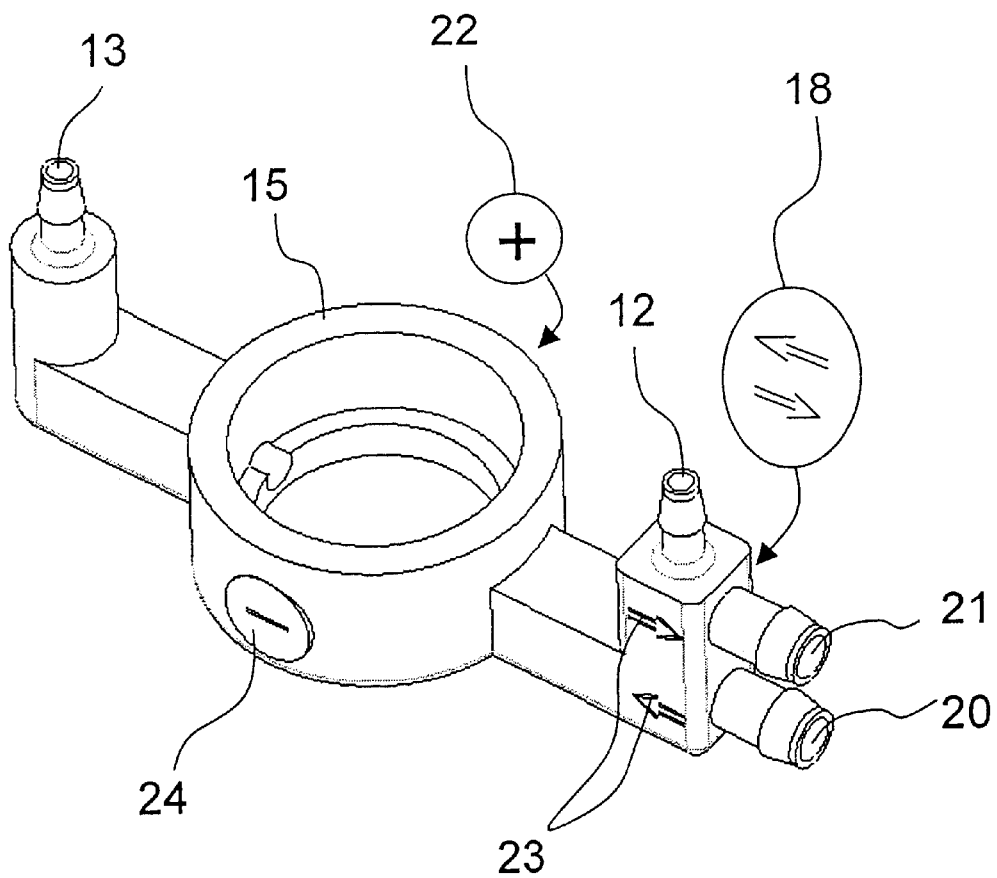
FIG. 5 is a perspective view of the plug-in adapter.

FIG. 5 shows a perspective view of the plug-in adapter 6 with the mounting sites for the arrows 18, 23, as well as the symbols 22, 24. Depending on the position of the plug-in adapter 6 on the measuring head, the user can immediately recognize by the symbols 22, 24 whether the sensor 5 is impacted by the measured gas in the suction operation or in the pressure operation.

While specific embodiments of the invention have been shown and described in detail to illustrate the application of the principles of the invention, it will be understood that the invention may be embodied otherwise without departing from such principles.

What is claimed is:

1. A device for gas analysis, the device comprising:
   a sensor;
   a measured gas pump;
   a plug-in adapter that can be connected with said measured gas pump and said sensor, said plug-in adapter having a first measuring channel that is in flow connection with a gas-sensitive surface of said sensor, said plug-in adapter being connected with said measured gas pump in either one of two positions in such a way that a connecting branch of said first measuring channel is connected in a first position of said plug-in adapter on a pressure side of said measured gas pump and in a second position on a suction side of said measured gas pump.

2. A device in accordance with claim 1, wherein said sensor and said measured gas pump are accommodated in a measuring head with plug sockets arranged on a connecting surface facing towards said plug-in adapter for connecting with said suction side and said pressure side as well as said gas-sensitive surface of said sensor.

3. A device in accordance with claim 2, wherein said plug sockets and said sensor are positioned on said connecting surface such that said plug-in adapter can be placed on said measuring head, adapting to any change.

4. A device in accordance with claim 2, wherein said plug-in adapter has a second measuring channel to be connected with said plug socket of said measured gas pump not occupied by said first measuring channel.

5. A device in accordance with claim 2, further comprising a switching element which determines the position of said plug-in adapter, said switching element being provided on said measuring head.

6. A device for gas analysis, the device comprising:
   a support;
   a sensor with a gas-sensitive surface, said sensor being connected to said support;
   a measured gas pump connected to said support, said gas pump having a pressure side connection and a suction side connection;
   a plug-in adapter with plug in parts for connection with said support and having a first measuring channel that is in flow connection with a gas-sensitive surface of said sensor in a plug in position and a second measuring channel and with a connecting branch of said first measuring channel, said connecting branch being connected by one of said plug in parts on one of said suction side of said measured gas pump and said pressure side of said measured gas pump and said second measuring channel being connected by the other of said plug in parts on the other of said suction side of said measured gas pump and said pressure side of said measured gas pump.

7. A device in accordance with claim 6, wherein support for said sensor and said measured gas pump is a measuring head with plug sockets arranged on a connecting surface facing towards said plug-in adapter for receiving respective plug in parts for connecting said plug-in adapter with said suction side and said pressure side as well as said gas-sensitive surface of said sensor.

8. A device in accordance with claim 7, wherein said plug sockets and said sensor are positioned on said connecting surface such that said plug-in adapter can be placed on said measuring head, adapting to any change.

9. A device in accordance with claim 2, further comprising a switching element which determines the position of said plug-in adapter, said switching element being provided on said measuring head.

10. A device for gas analysis, the device comprising:
a support;
a sensor with a gas-sensitive surface, said sensor being connected to said support;
a measured gas pump connected to said support, said gas pump having a pressure side connection and a suction side connection;
a plug-in adapter with a plug in part for connection with said support and having a first measuring channel that is in flow connection with a gas-sensitive surface of said sensor in a plug in position and with a connecting branch of said first measuring channel, said connecting branch being connected by said plug in part on one of said suction side of said measured gas pump and said pressure side of said measured gas pump.

* * * * *